United States Patent [19]

Saville

[11] Patent Number: Plant 7,032

[45] Date of Patent: Sep. 19, 1989

[54] MINIATURE ROSE PLANT NAMED SAVACOP

[75] Inventor: F. Harmon Saville, Newburyport, Mass.

[73] Assignee: Nor'East Miniature Roses, Rowley, Mass.

[21] Appl. No.: 257,523

[22] Filed: Oct. 14, 1988

[51] Int. Cl.[4] ..... A01H 5/00

[52] U.S. Cl. ..... Plt./7

[58] Field of Search ..... Plt./7

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A new and unusual miniature rose with copper-orange to copper-red flowers.

1 Drawing Sheet

SUMMARY OF THE INVENTION

The present invention relates to a new and distinct variety of rose plant of the miniature rose class, which was originated by my crossing as seed parent the variety known as "Acey Deucy" (U.S. Plant Pat. No. 5,092) and as pollen parent the rose known as "Rainbow's End" (U.S. Plant Pat. No. 5,482). The denomination of this new rose is "Savacop".

Among the novel characteristics possessed by this new variety which distinguish it from its parents and all other varieties of which I am aware are its unusual, bright copper-orange to copper-red flowers in this class of rose. Flowers are long lasting on the plant and after cutting. Asexual reproduction by propagation by cuttings of the new variety as performed in San Bernardino County, Calif. shows that the foregoing and other distinguishing characteristics come true to form and are established and transmitted through succeeding propagations.

BRIEF DESCRIPTION OF DRAWING

The accompanying drawing shows typical specimens of the vegetative growth and flowers of the new variety in different stages of development and depicted in color as nearly true as it is reasonably possible to make the same in a color illustration of this character.

DESCRIPTION OF PREFERRED EMBODIMENT

The following is a detailed description of my new variety, with color terminology in accordance with The Royal Horticultural Society Colour Chart (RHSCC). The terminology used in color description herein refers to plate numbers in the aforementioned color chart, e.g., "170D" is plate 170D of The Royal Horticultural Society Colour Chart.

Parentage: Seedling.

*Seed parent.*—"Acey Deucy".

*Pollen parent.*—"Rainbow's End".

Class: Miniature.

The following observations are made of specimens grown outdoors in San Bernardino County, Calif., during the month of April.

Flower

Blooming habit: Nearly continuous.

A. Bud:

(1) *Size.*—Medium.

(2) *Form.*—Long pointed, high centered. '(3) *Color*.—As sepals break, but color is near 34A becoming near 170D to 170A flushed with near 44C as sepals divide.

(4) Sepals.—Slightly foliated, longer than bud.

(5) *Peduncle.*—Length — about ½-inch. Aspect — straight. Strength — erect. Color — near 180A.

B. Bloom:

(1) *Size.*—Average size when fully expanded — about 1⅛-inch.

(2) *Borne.*—Singly, one to a stem and a few to many (5 to 20) in small and large sprays.

(3) *Form.*—High centered at first, becoming flat. Outer petals reflex and quill to points; inner petals roll loosely under, becoming ruffled at maturity.

(4) *Petalage.*—Number of petals under normal conditions — about 21.

(5) *Color.*—After sepals fall and petals unfurl, coloring of outer petals tends toward near 170A to 170D with greyed red coloring, near 179B, infused on the petal top surface and near 179B predominating toward apices and petal edges of outer petals. Top surfaces of inner petals become more pronounced in near 170A to 170D, lightening in tonality in petals toward flower centers. Coloring of petal undersurfaces darkens from outer petals to inner petals with outer petals showing more 44C coloring and inner petals becoming near 179B to 179A. As blooms age, tan coloring lightens and greyed red coloring darkens. General tonality of fresh flowers from a distance appears as unusual copper-orange to orange-red.

C. Petals:

(1) *Texture.*—Medium to thick.

(2) *Appearance.*—Inside velvety and outside satiny.

(3) *Form.*—Broad, fan shaped, somewhat spatulate.

(4) *Arrangement.*—Regularly arranged, imbricated.

(5) *Petaloids in center.*—Few.

(6) *Persistence.*—Drop off cleanly.

(7) *Fragrance.*—Slight.

(8) *Lasting quality.*—Long lasting on plant and as cut flower.

REPRODUCTIVE ORGANS

A. Stamens, filaments and anthers: p2 *Arrangement and color.*—Regularly arranged around styles. Color — Filaments near 15A B. Pollen:
*Color.*—Near 15A.

C. Styles: Medium length.

D. Stigmas:
*Color.*—Near 2C.

E. Hips: Globular, ⅜-inch O.D.
*Color.*—Orange; seeds do not protrude.

PLANT

A. Form: Upright, somewhat angular.

B. Growth: Very vigorous.
*Height attained.*—About 14 to 16 inches.

C. Foliage: Compound 5 to 7 leaflets.
(1) *Size.*—Medium.
(2) *Quantity.*—Abundant.
(3) *Color.*—New Foliage: Upper side — near 137B. Under side — near 138B. Old foliage: Upper side — near 139A. Under side — near to 137C.
(4) *Shape.*—Oval, pointed.
(5) *Texture.*—Upper side is semi-glossy; under side is matte.
(6) *Edge.*—Serrate.

(7) *Serration.*—Ordinary.
(8) *Leaf stem.*—Color — near 147B. Under side — near 147C.
(9) *Stipules.*—Long, smooth.
(10) *Resistance to disease.*—Blackspot — Average. Mildew — Average. Rust — Average.

D. Wood:
(1) *New wood.*—Color — near 144A. Bark — smooth.
(2) *Old wood.*—Color — near 144A. Bark — smooth.

E. Thorns:
(1) *Thorns.*—Quantity (main stalk) — ordinary. On laterals from stalk — few; slanted sharply downward. Length — short. Color — near 182B. Position — irregular.
(2) *Prickles.*—None.

F. Winter hardiness: Needs protection in severe climates.

I claim:

1. A new and distinct variety of rose plant of the miniature rose class, and parts thereof, substantially as shown and described, characterized particularly by attractive flowers of unusual copper-orange to copper-red coloring.

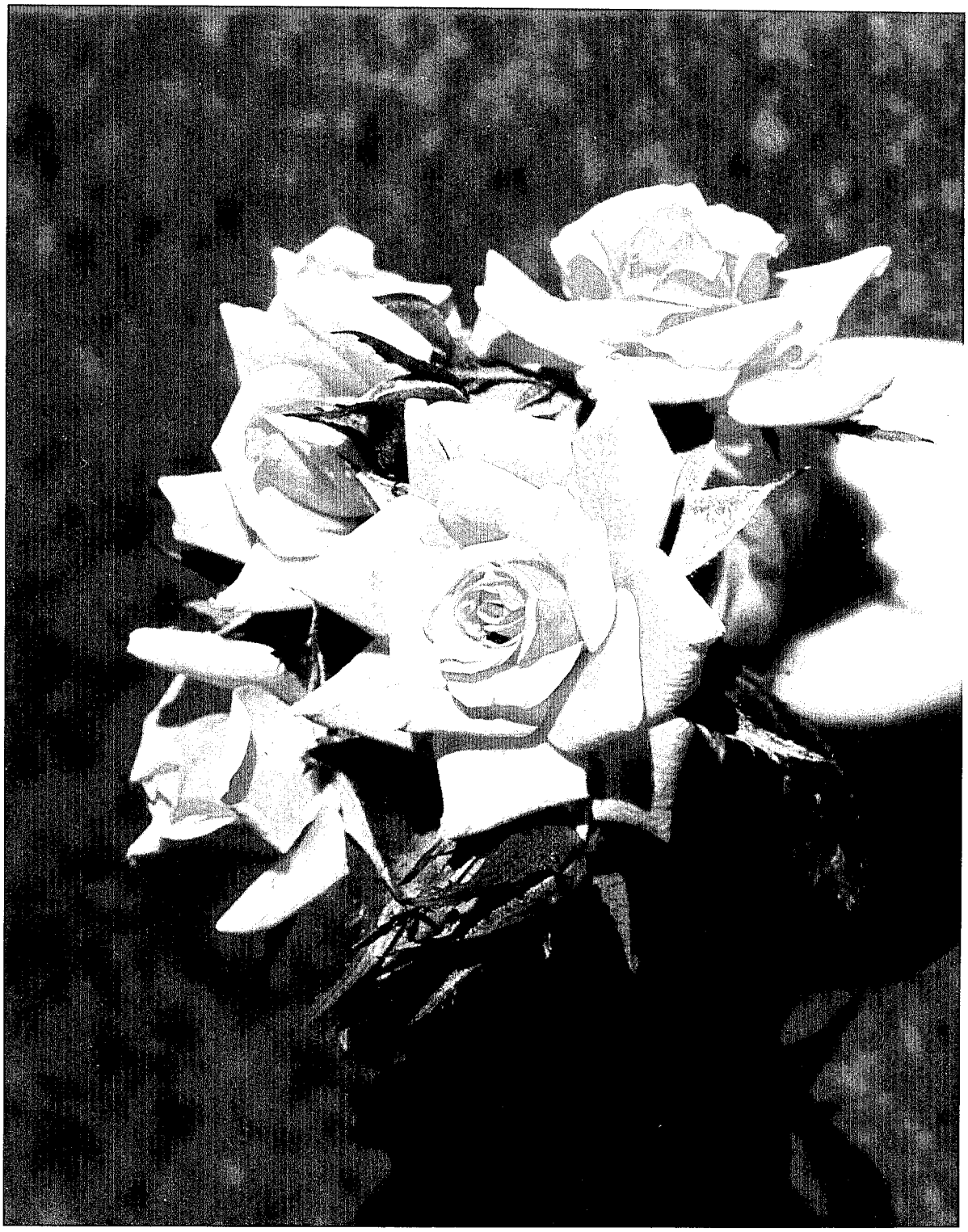

* * * * *